(12) United States Patent
Busse et al.

(10) Patent No.: US 9,330,890 B2
(45) Date of Patent: May 3, 2016

(54) ELECTRODE ARRANGEMENT FOR A DIELECTRICALLY LIMITED GAS DISCHARGE

(75) Inventors: Benedikt Busse, Göttingen (DE);
Leonhard Trutwig, Duderstadt (DE);
Maximilian Segl, Duderstadt (DE); Dirk Wandke, Heilbad Heiligenstadt (DE);
Matthias Kopp, Gieboldenhausen (DE);
Michael Nolte, Seeburg (DE); Johannes Scharf, Bergisch-Gladbach (DE);
Karl-Otto Storck, Duderstadt (DE)

(73) Assignee: CINOGY GmbH, Duderstadt (DE)

( * ) Notice: Subject to any disclaimer, the term of this patent is extended or adjusted under 35 U.S.C. 154(b) by 136 days.

(21) Appl. No.: 14/127,316

(22) PCT Filed: Jun. 6, 2012

(86) PCT No.: PCT/DE2012/000602
§ 371 (c)(1),
(2), (4) Date: Dec. 18, 2013

(87) PCT Pub. No.: WO2012/175066
PCT Pub. Date: Dec. 27, 2012

(65) Prior Publication Data
US 2014/0182879 A1 Jul. 3, 2014

(30) Foreign Application Priority Data
Jun. 23, 2011 (DE) .......................... 10 2011 105 713

(51) Int. Cl.
*H01J 37/32* (2006.01)
*A61N 1/40* (2006.01)
*H05H 1/24* (2006.01)

(52) U.S. Cl.
CPC ............. *H01J 37/32541* (2013.01); *A61N 1/40* (2013.01); *H05H 1/2406* (2013.01); *H05H 2001/2418* (2013.01); *Y10T 29/49204* (2015.01)

(58) Field of Classification Search
CPC .......................... H05H 1/2406; H01J 37/32541
USPC ................................. 174/98, 117 F, 117 FF
See application file for complete search history.

(56) References Cited

U.S. PATENT DOCUMENTS

| 4,652,318 A | 3/1987 | Masuda et al. |
| 5,648,701 A * | 7/1997 | Hooke et al. ............. 315/111.21 |

(Continued)

FOREIGN PATENT DOCUMENTS

| DE | 19532105 A1 | 3/1996 |
| DE | 100 47 688 | 10/2004 |
| DE | 102007030915 A1 | 1/2009 |

(Continued)

*Primary Examiner* — William H Mayo, III
*Assistant Examiner* — Hiram E Gonzalez
(74) *Attorney, Agent, or Firm* — Whitham, Curtis, Christofferson & Cook, P.C.

(57) ABSTRACT

The invention relates to a flexible flat electrode arrangement for a dielectrically limited gas discharge, comprising a central region (3), an edge region, and a flat electrode (14) which conducts a high-voltage potential and which is embedded in a flat dielectric that forms an upper face (10) and a contact face (6). The invention allows the active surface of the electrode arrangement to be matched to the size of a surface to be treated in that the flat dielectric is in the form of a flat strip (1) wound into a spiral at least in the edge region, and the electrode (14) is formed by at least one electric conductor which runs in the longitudinal direction of the wound strip (1) and which leads into an end surface (13) of the strip (1).

9 Claims, 9 Drawing Sheets

(56) References Cited

U.S. PATENT DOCUMENTS

| | | | |
|---|---|---|---|
| 5,909,086 A * | 6/1999 | Kim et al. | 315/111.21 |
| 7,008,596 B1 * | 3/2006 | Rump et al. | 422/186.07 |
| 2002/0084180 A1 | 7/2002 | Schmidt-Boecking et al. | |
| 2009/0159309 A1 * | 6/2009 | Kanada et al. | 174/117 F |
| 2011/0022043 A1 | 1/2011 | Wandke et al. | |
| 2012/0271225 A1 | 10/2012 | Stieber et al. | |
| 2013/0064726 A1 * | 3/2013 | Morfill et al. | 422/186.21 |

FOREIGN PATENT DOCUMENTS

| | | |
|---|---|---|
| DE | 10 2008 006 256 | 7/2009 |
| DE | 20 2009 011 521 | 2/2011 |
| WO | WO 98/49368 | 11/1998 |
| WO | WO 01/02291 | 1/2001 |

* cited by examiner

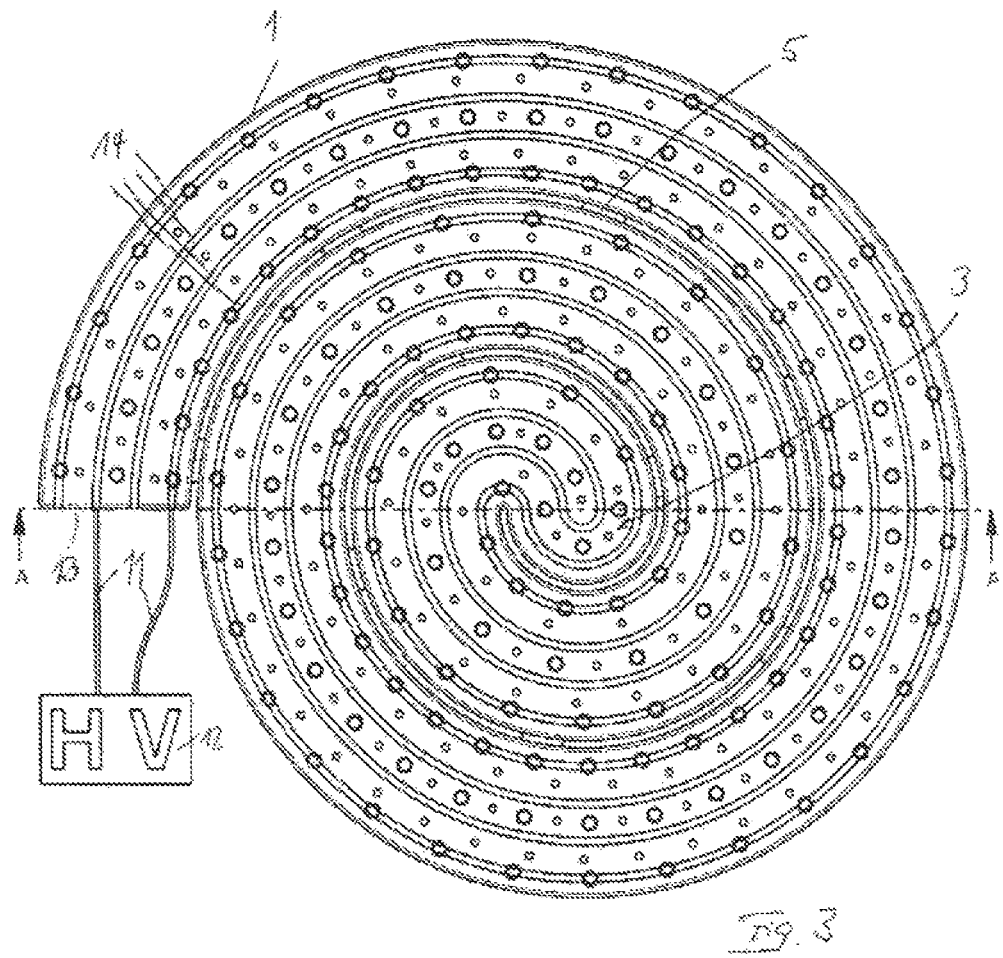
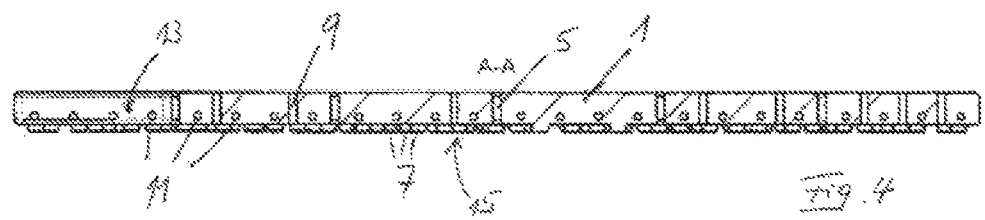

ELECTRODE ARRANGEMENT FOR A DIELECTRICALLY LIMITED GAS DISCHARGE

FIELD OF THE INVENTION

The invention relates to a flexible, flat electrode arrangement for a dielectric barrier gas discharge.

BACKGROUND

Dielectric barrier plasma discharges are used for numerous applications. DE 195 32 105 C2 discloses treating, for example activating or cleaning, the surface of three-dimensional workpieces. By virtue of a so-called barrier discharge, it is possible to reduce a layer of oil to minimum quantities of oil per unit length. It is essential here, however, that uniform treatment of the surface takes place. For this, a homogeneous formation or the plasma is required, wherein the idea consists in that the plasma discharges take place in thin filaments which are spaced apart from one another. This is problematic in the case of surfaces with an irregular three-dimensional shape. Therefore, DE 195 32 105 C2 provides for a negative form with the dielectric to be formed by the surface of the workpiece, which negative form therefore consists of a shapeable, for example pressable or deep-drawable plastic. Provision is also made here for an intermediate layer to be used, with the result that the dielectric can be shaped with the intermediate layer directly on the surface of the workpiece. The intermediate layer is then removed in order to ensure an interspace between the dielectric and the electrode, in which the plasma can form. On its side facing away from the surface to be treated, the dielectric is coated with a conductive material, to which the required high voltage in the form of an AC voltage can be supplied.

DE 10 2007 030 915 A1 discloses forming hollow fibers from a dielectric material, which hollow fibers are provided with a metallically conductive coating in the interior of said hollow fibers, with the result that the hollow fibers form a dielectric with an inner shielded electrode which, together with the surface acting as mating electrode of a conductive body, can form a plasma field. In this case, provision is also made for a fabric to be formed with hollow fibers which can be laid flat onto an irregular surface, in particular surface of the skin of a human body. This results in the advantage of an electrode arrangement which can be matched to the irregular topology of the surface of the skin for performing a plasma treatment. However, one disadvantage with this consists in the high manufacturing complexity for the formation of the hollow fibers forming the fabric, which hollow fibers are intended to have a flexible electrode in their cavity in order no ensure the flexibility of the electrode fabric required for matching to the surface of the skin.

SUMMARY

According to the invention, a dielectric barrier gas discharge or plasma treatment is also intended to be possible for bodies with as irregular three-dimensional shape, in particular also for the surface of the skin of a living organism. In this case, the surface to be treated can act as mating electrode by virtue of it being connected electrically to ground, for example. However, it is also possible to form a dedicated mating electrode with the electrode arrangement, with the result that a dielectrically impeded plasma treatment for flat bodies with an irregular shape is also possible in an intermediate space between the electrode arrangement and the mating electrode.

A problem in terms of production technology consists for the flat electrodes is that the size of the surface to be treated is often not known in advance. It is therefore known to produce flat electrodes in predetermined, possibly several, sizes. In this case, if appropriate, a discrepancy between the size of the electrode and the size of the surface to be treated needs to be accepted. In order to treat the entire surface, if appropriate the electrode arrangement needs to be laid several times in different positions. If in the reverse case the laid electrode arrangement is too large for the surface to be treated, an unnecessarily large field for the generation of the plasma is built up.

Therefore, the present invention is based on the object of providing a flat, flexible electrode arrangement which can be produced easily and inexpensively and, in terms of its effective area, can be matched easily to the size of the surface to be treated.

This object is achieved according to the invention by a flexible, flat electrode arrangement comprising a central region and a peripheral region and comprising a flat electrode conducting a high voltage potential, which electrode is embedded in a flat dielectric forming an upper side and a resting side. The flat dielectric has, at least in the peripheral region, the form of a flat strip wound in helical fashion, and the electrode is formed by at least one electrical conductor which runs in the longitudinal direction of the wound-up strip and opens out into an end face of the strip.

The flat electrode arrangement according to the invention can therefore be produced in a maximum required size and, for a specific application case, reduced in size by virtue of the fact that a piece of the helically wound strip is cut to length. The electrode formed by the at least one electrical conductor extends into the end face of the strip and contact can be made with said electrode safely and reliably at the end of the strip in order to ensure the connection to the high voltage source. For this, it is conceivable to remove the insulation from one electrical conductor by removing the flat dielectric in order then to produce a contact with conventional connection means. However, it is preferred to keep the dielectric unchanged and to produce the contact with the aid of insulation displacement contacts, which cut through the dielectric in the end region of the strip from a large surface in order thus to produce a metallic contact with the electrical conductor. Such a contact arrangement has the advantage that safe insulation of the electrode arrangement with respect to the high voltage supplied to the electrical conductor is ensured in a simple manner.

The electrical conductor embedded in the flat dielectric can have numerous embodiments. It is thus possible, for example, to embed the conductor as a metallic grid-like strip in the helically wound flat dielectric strip.

In an embodiment that is advantageous in terms of production technology, the conductor is at least one narrow conductor running in the strip from the end face to the central region and from there back to the end face. Such a narrow conductor, in particular when it is in the form of a conductor wire with a round or oval cross section, can easily be matched to the curvature of the helically round dielectric strip and can furthermore make contact in a simple manner in the same way as a core of an electrical cable. Contact is preferably made with the electrode according to the invention in the region of the end face with a contact arrangement and the electrode is electrically insulated from the surrounding environment. This is achieved in a simple manner with a contact arrangement known per se, which has a housing which is open on one side and into which the end face of the helically wound strip is pushed in such a way that the housing surrounds in insulating fashion the end face, an upper side and lower side and narrow side of an end region of the strip, which end region is adjacent to the end face, and the contact arrangement is provided with insulation displacement contacts for making contact with the flat electrode, which insulation displacement contacts penetrate into the dielectric in self-cutting fashion from the upper side and/or the lower side.

The flexible flat electrode arrangement according to the invention in a preferred embodiment is designed to rest on a surface to be treated, wherein the surface forms a mating electrode with respect to an electrode which is contained in the electrode arrangement and conducts a high voltage. It is advantageous here if the strip has integrally formed elevations on its resting side, which elevations define a resting plane and have interspaces which are suitable as the gas space for forming a plasma. The plasma is therefore produced in the interspaces between the elevations of the dielectric. In a further preferred embodiment, the strips have through-openings which pass through the dielectric from the resting side to the upper side and are preferably connected to a suction removal device for fluids from the gas space formed by the interspaces. As a result, it is possible in particular for a plasma treatment of a wound surface to be performed and, for example, for secretions from the wound to be removed by suction via the through-opening during the plasma treatment. It is of course also conceivable for suitable materials to be introduced into the plasma space between the elevations, in particular gaseous materials, via the through-opening.

The electrode arrangement according to the invention also makes it possible to form a dedicated mating electrode which is part of the electrode arrangement.

BRIEF DESCRIPTION OF THE DRAWINGS

The arrangement will be explained in more detail below with reference to the exemplary embodiments illustrated in the drawing, in which:

FIG. 3 shows a plan view of the resting side of the electrode shown in FIG. 1 with an illustration of the conductor wires which run in the interior of the electrode arrangement and form an electrode;

FIG. 4 shows a section along the line A-A on FIG. 3;

DETAILED DESCRIPTION

Figure 1:
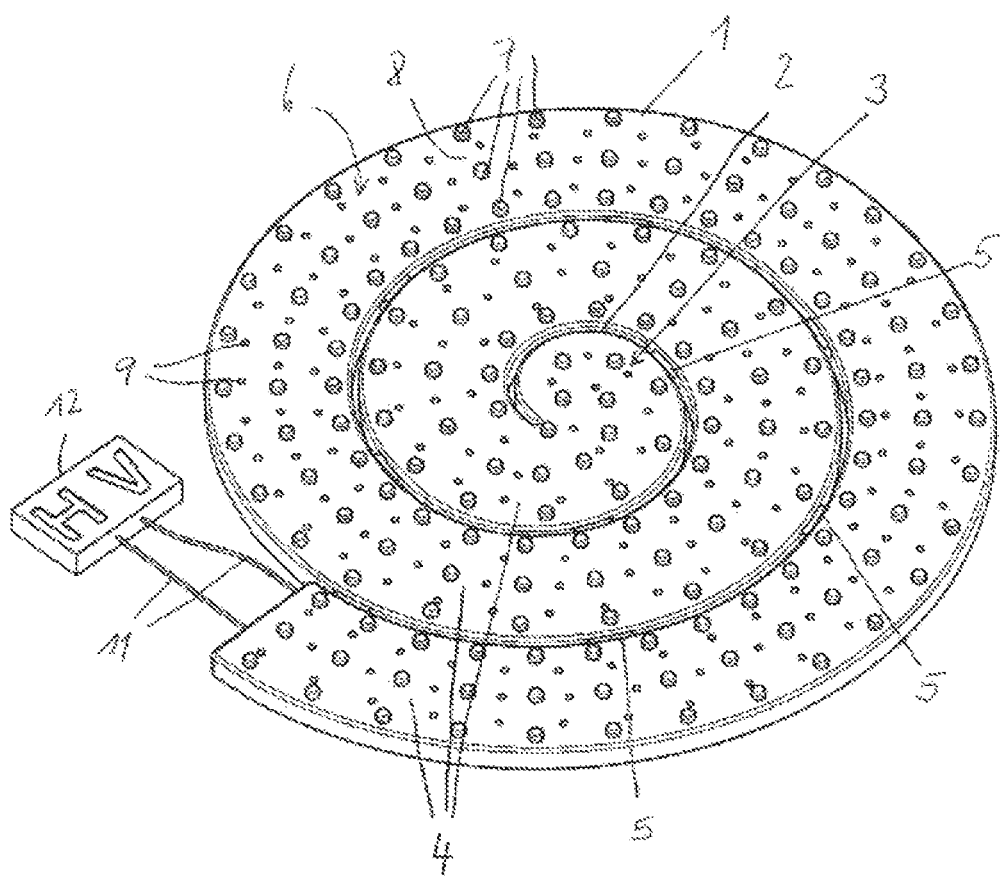
FIG. 1 shows a schematic perspective view of a resting side of the electrode arrangement with a schematically illustrated connection to a high-voltage supply.

In the first embodiment of a flat electrode arrangement according to the invention illustrated in FIG. 1, said electrode arrangement comprises a helically wound flat strip 1, which, with a rounded-off end 2, forms a central region 3 of the electrode arrangement and is then shaped in such a way that it forms helical turns 4 resting against one another, by means of which turns a peripheral region is defined. The turns of the strip rest against one another via integrally formed spacer pieces 5.

The strip 1 consists of a dielectric material and forms a dielectric of the electrode arrangement. The side shown in FIG. 1 represents a resting side 6, on which the strip 1 is provided with a multiplicity or elevations 7, which in the exemplary embodiment illustrated are in the form of round knobs. The elevations 7 all have the same height and, with their upper side, define a resting surface for a mating electrode (not illustrated), which can be formed by the surface to be treated when said surface is connected to ground, for example. The elevations 7 only take up a small surface area component of the resting surface 6, with the result that a much greater proportion of the resting surface consists of interspaces 8 between the elevations 7. The surface proportion of the elevations can be between 5 and 40% of the resting surface 6, while the interspaces 8 take up a surface proportion of 60 to 95%, preferably between 75 and 95%.

FIG. 1 also shows that small through-openings 9 have been introduced in the strip 1, which through-openings are preferably distributed uniformly over the surface of the strip. The through-openings 9 extend from the resting side 6 toward the opposite upper side 10 (cf. FIG. 2). The through-openings 9 advantageously enable removal by suction of fluid from the interspaces 8 in which a plasma is intended to form during operation of the electrode arrangement.

For the formation of the plasma, an electrode, which is represented schematically as being connected to a high voltage supply 12 by means of two conductor wires 11 in FIG. 1, is embedded in the dielectric formed by the strip 1.

Figure 2:
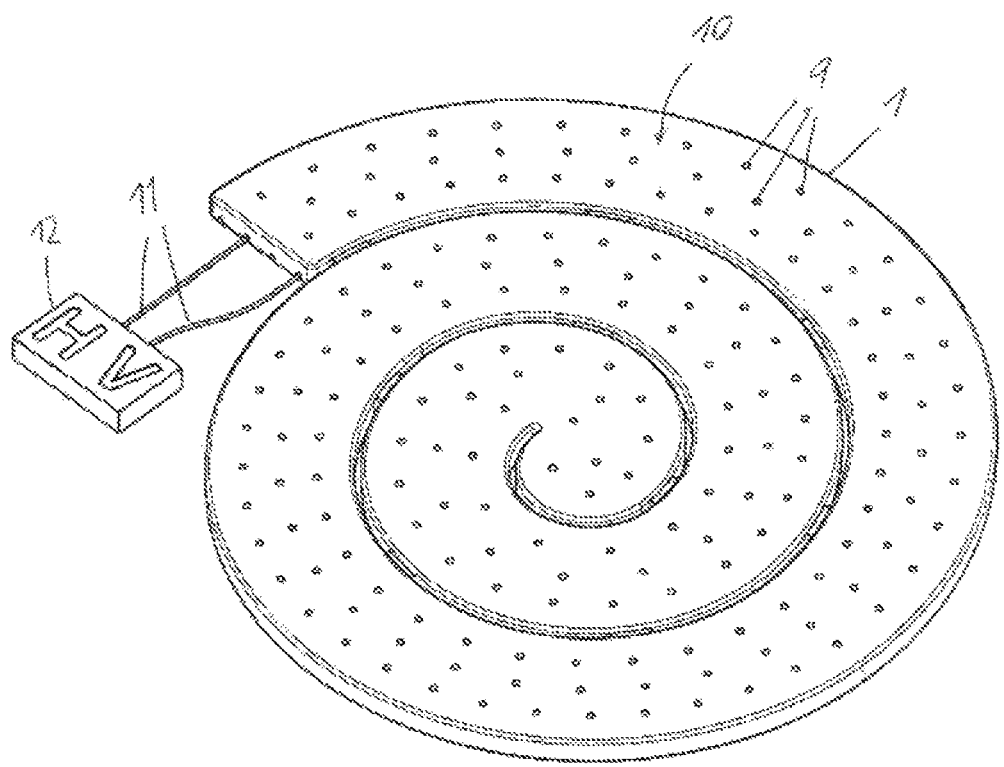
FIG. 2 shows a schematic perspective view of an upper side of the electrode arrangement shown in FIG. 1.

FIG. 2 shows a view of the upper side 10 of the electrode arrangement formed by the strip 1. Only the through-openings 9 are visible from the upper side 10.

The illustration in FIG. 3 shows that the conductor wires 11 run within the strip 1 in the longitudinal direction thereof, to be precise as far as into the central region 3 formed by the rounded-off end 2 of the strip 1. In the central region 3, the conductor wires are bent through 180° so as to match the rounded-off end 2 and run parallel to one another through the conductor back to an end face 13. The end face 13 represents the outer free end of the strip 1 and can be aligned at right angles (radially) with respect to the longitudinal extent of the strip 1. However, it is also possible for the end face to be formed with any desired angle with respect to the longitudinal extent of the strip 1.

FIG. 3 shows that the two conductor wires 11 which run to and fro in the longitudinal direction of the strip 1 form an electrode 14 which is embedded in the dielectric formed by the strip and which is therefore formed by four sections of the conductor wires 11 running parallel to one another in the exemplary embodiment illustrated.

The conductor wires 11 of the electrode 14 are connected to an identical high-voltage potential in the high-voltage supply 12. They therefore form an electrode connected to a high-voltage potential which, with a mating electrode which is formed, for example, by the surface to be treated which is connected to ground, a treatment space which is formed in the case of the electrode illustrated by the interspaces 8 between the elevations 7. The electrode 14 is delimited on all sides by the dielectric of the strip 1, with the exception merely of the end face 13.

In the case of the connection of the conductor wires 11 to the high-voltage supply 12 as illustrated schematically in FIGS. 1 to 3, insulation of the conductor wires 11 is of course required outside of the end face 13 in the same way as is required at the end face 13 itself.

The sectional illustration in FIG. 4 shows a view of the end face 13, and also the interspace running in helical fashion and formed by the spacer pieces 5 between the turns 4 of the strip 1 and the multiplicity of elevations 7, whose identical heights form a resting plane 15.

Figure 5:
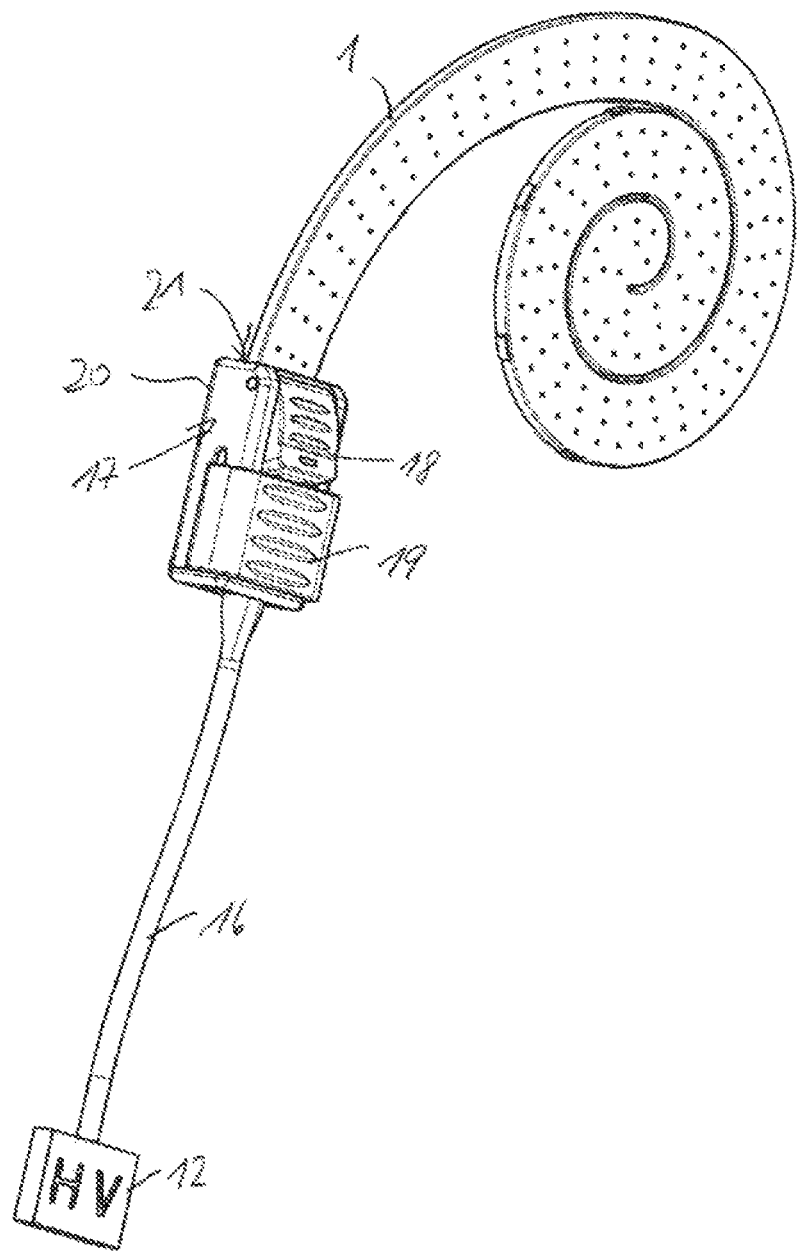
FIG. 5 shows a schematic perspective illustration of a further exemplary embodiment of a flat electrode arrangement comprising a special contact-making element for making contact with the conductor wires running through the strip forming the electrode arrangement in the region of an end face.

Contact-making of the conductor wires 11 running within the strip, which contact-making is not only schematic but also realistic, is illustrated in FIG. 5. In this case, the high-voltage supply 12 is connected to a contact-making element 17 via an insulated high-voltage cable 16, which contact-making element 17 has a pivotably mounted holder 8 and a locking slide 19. The holder 18 and the locking slide 10 are located on a housing 20, which is closed in insulating fashion on all sides and has an insertion slot 21 for an end region of the strip having the end face 13. FIG. 5 illustrates that the end region of the strip has been inserted into the insertion slot 21.

Figure 6:
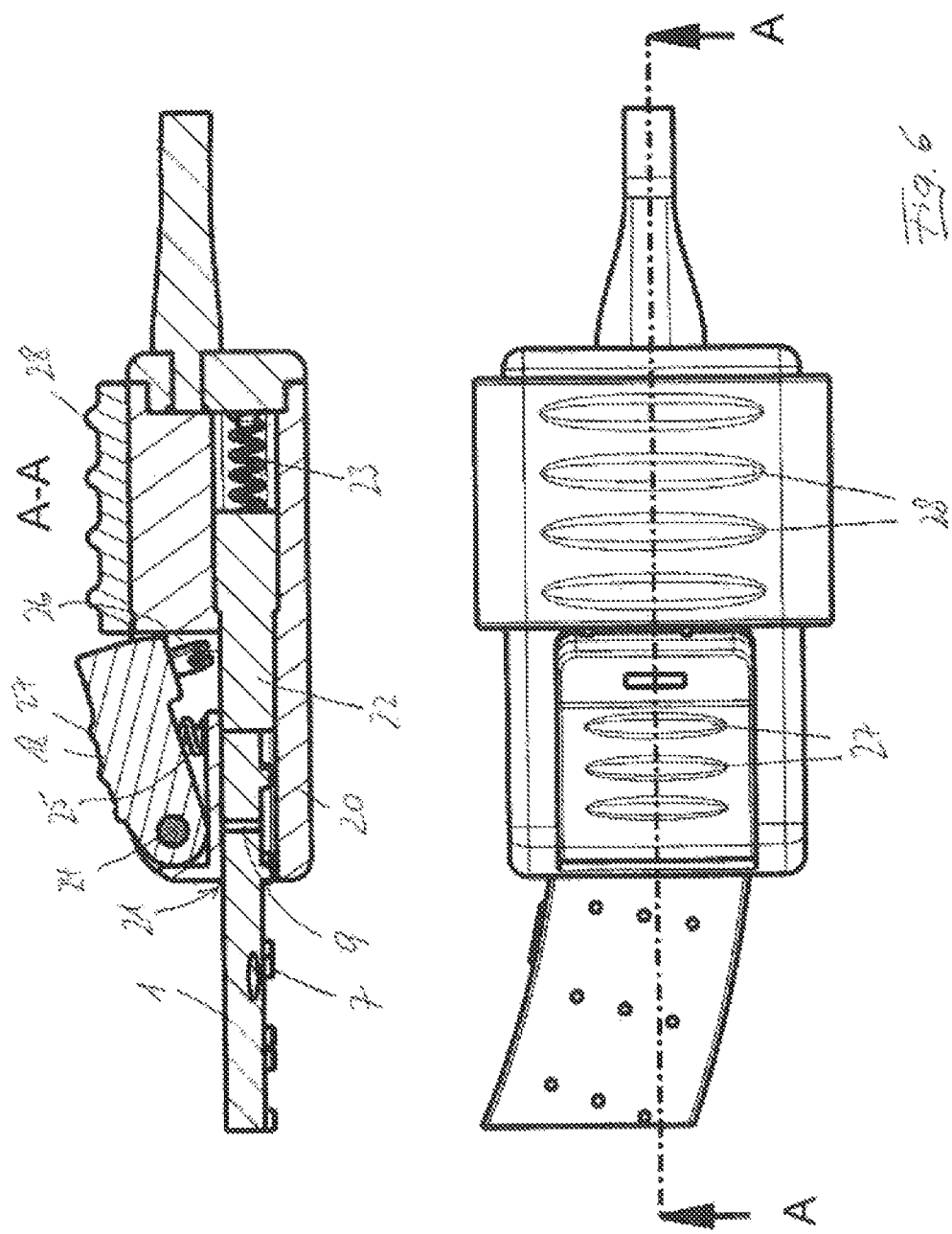
FIG. 6 shows a vertical section along the line A-A and a plan view of the contact-making arrangement in a first state.

The illustration in FIG. 6 shows the end region of the strip 1, which has been inserted into the insertion slot 21 of the housing 20 against a stop 22, which is mounted longitudinally displaceable in the housing 20 and is held in a rest position by a compression spring 23. The sectional illustration in FIG. 6 also shows that the pivotable holder 8 can be pivoted about a rotary spindle 24, which is aligned in parallel with the insertion slot 21, but transversely with respect to the longitudinal extent of the strip. A compression spring 25 presses the holder into a pivoted-up position illustrated in FIG. 6, in which metallic insulation displacement contacts 26 held at the end of the holder 18 on its lower side are above the stop 22.

FIG. 6 furthermore shows that both parallel ribs 27 are formed on the holder 18 and parallel ribs 28 are formed on the locking slide on the upper sides in order to facilitate manipulation.

Figure 7:
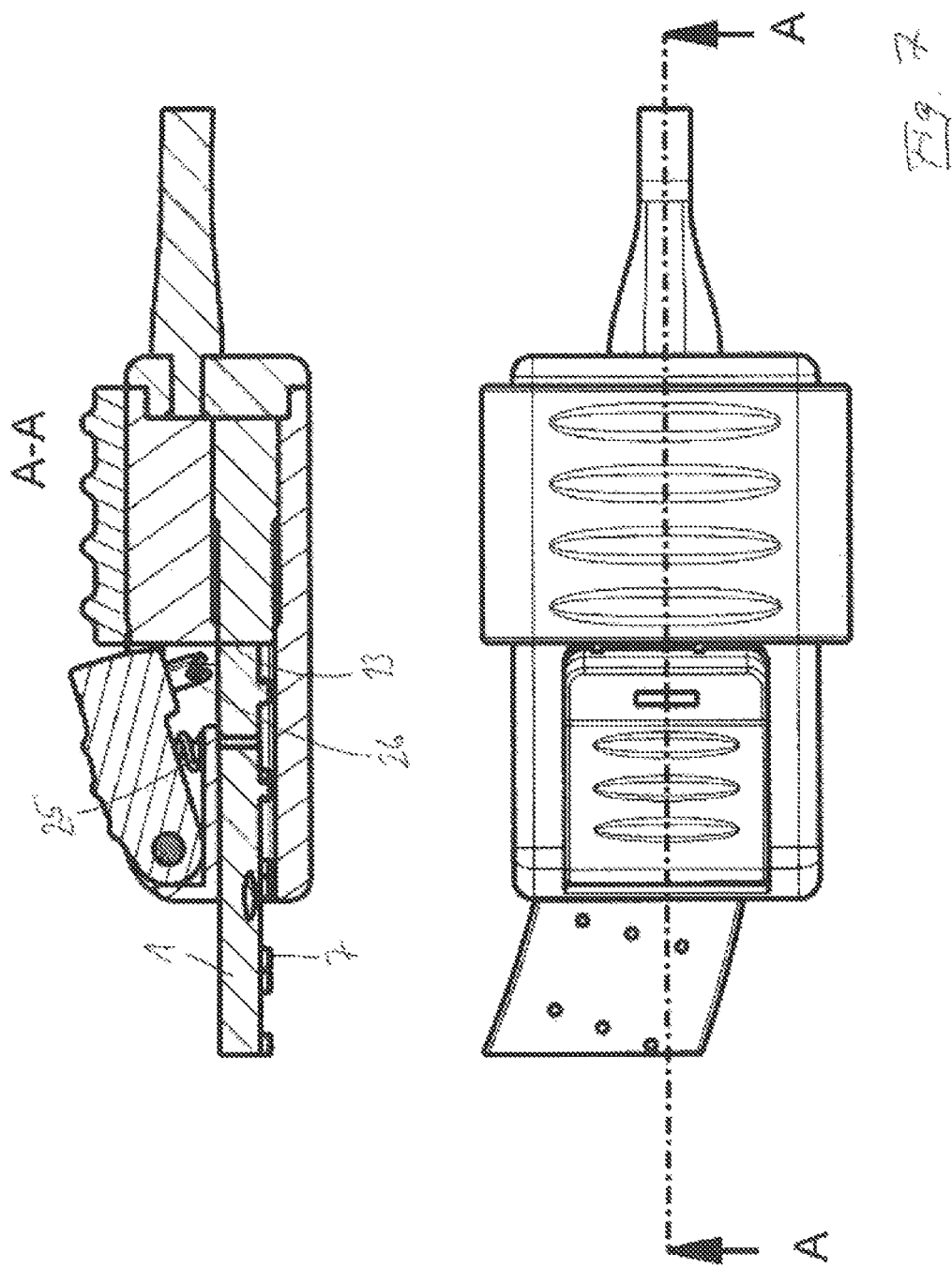
FIG. 7 shows an illustration of the contact-making arrangement shown in FIG. 6 in an inserted state of the strip.

FIG. 7 illustrates that, in comparison with the first position illustrated in FIG. 6, the strip 1 is inserted further into the insertion slot 21 and in the process presses the stop 22 axially in counter to the force of the compression spring 23 illustrated in FIG. 6 until the end of the strip 1 with the end face 13 pressing against the stop 22 comes to lie beneath the insulation displacement contacts 26.

Figure 8:
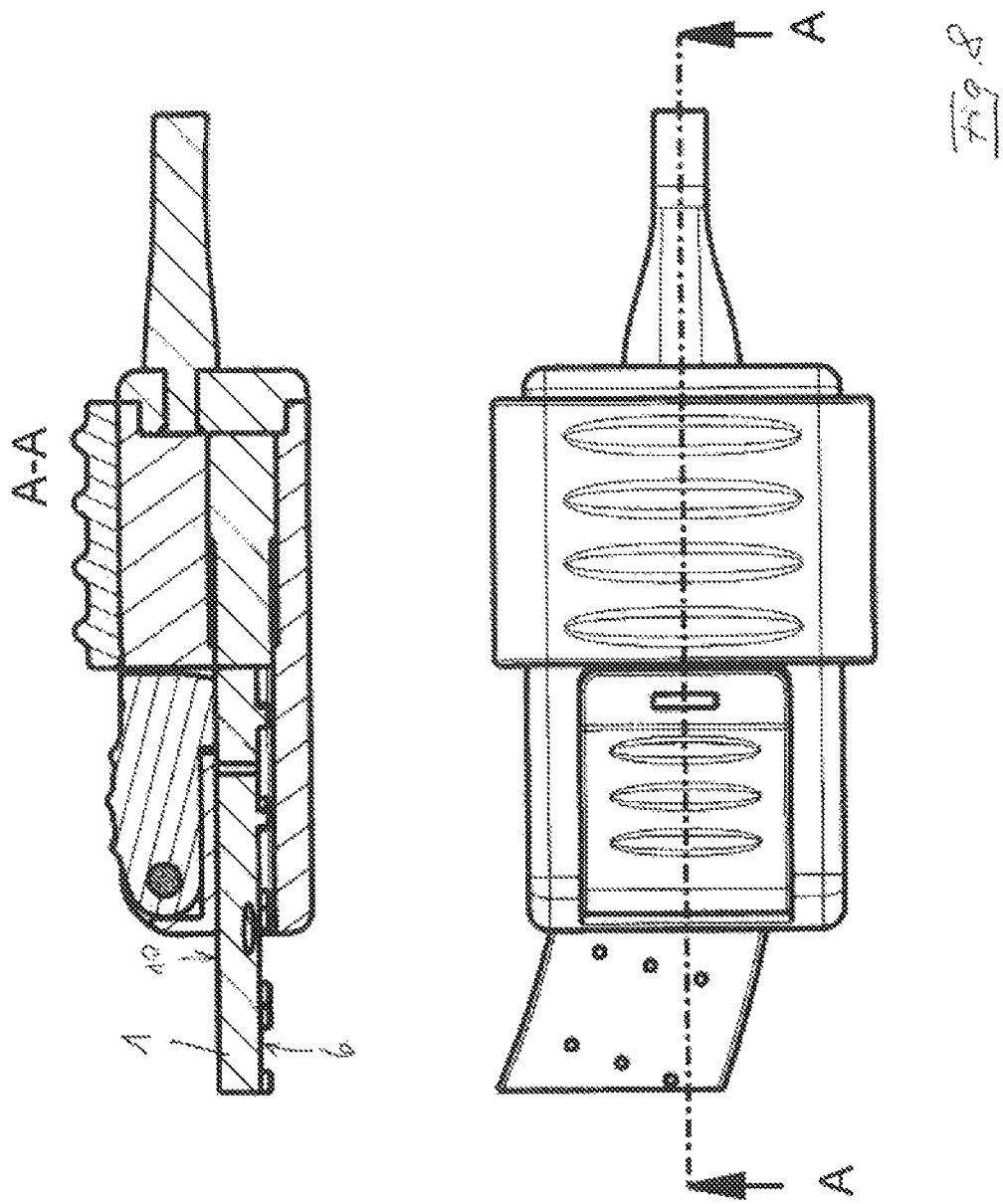
FIG. 8 shows an illustration of the contact-making arrangement shown in FIG. 7 in a folded-down position of a pivotable holder for insulation displacement contacts.
Figure 9:
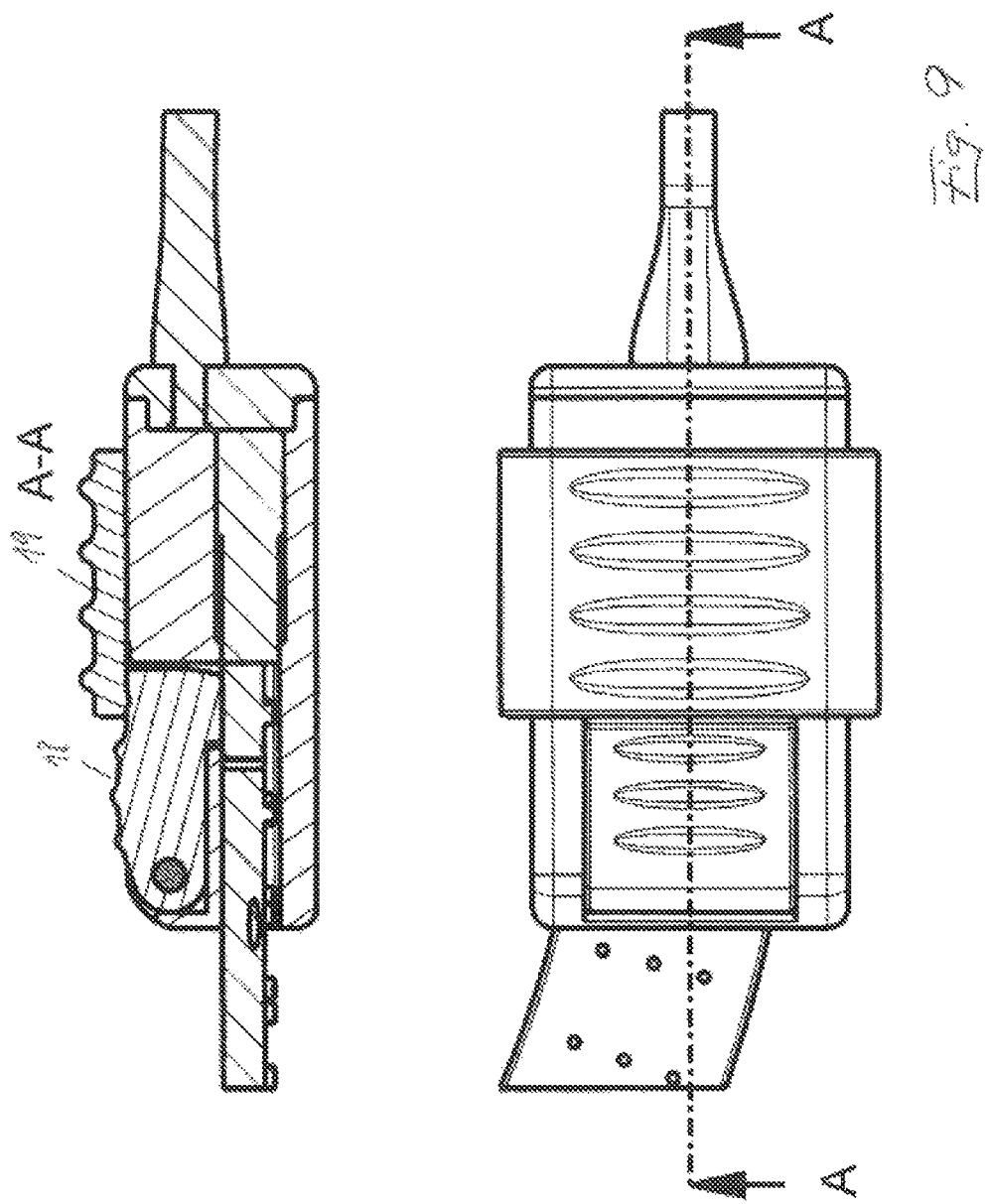
FIG. 9 shows an illustration as in FIG. 8, in which the pivotable holder is locked by a slide engaging over said pivotable holder.

FIG. 8 illustrates that the contact-making with the conductor wires 11 running within the strip 1 is now performed by virtue of the fact that the pivotable holder 18 is pivoted downwards by pressure being exerted on its upper side counter to the force of the compression spring 25, as a result of which the insulation displacement contacts 26 cut into the material of the strip 1 from the upper side 10 until a metallic, i.e. electrically conductive, connect is produced with the metallic conductor wires 11. Whilst maintaining the pressure on the holder 18, the locking slide 19 is moved in the longitudinal direction, as shown in FIG. 9, so that it now protrudes beyond the holder 18, with the result that said holder is locked in the contact-making position counter to the restoring force of the compression spring 23. The holder 18, the locking slide 9, the housing 20, etc. of the contact-making elements 17 of course consist of a nonconductive material, for example plastics, with the result that safe insulation is ensured on all sides and there is no risk of unimpeded dissipation of the high voltage by virtue of touching contact with parts of the electrode 14.

Figure 10:
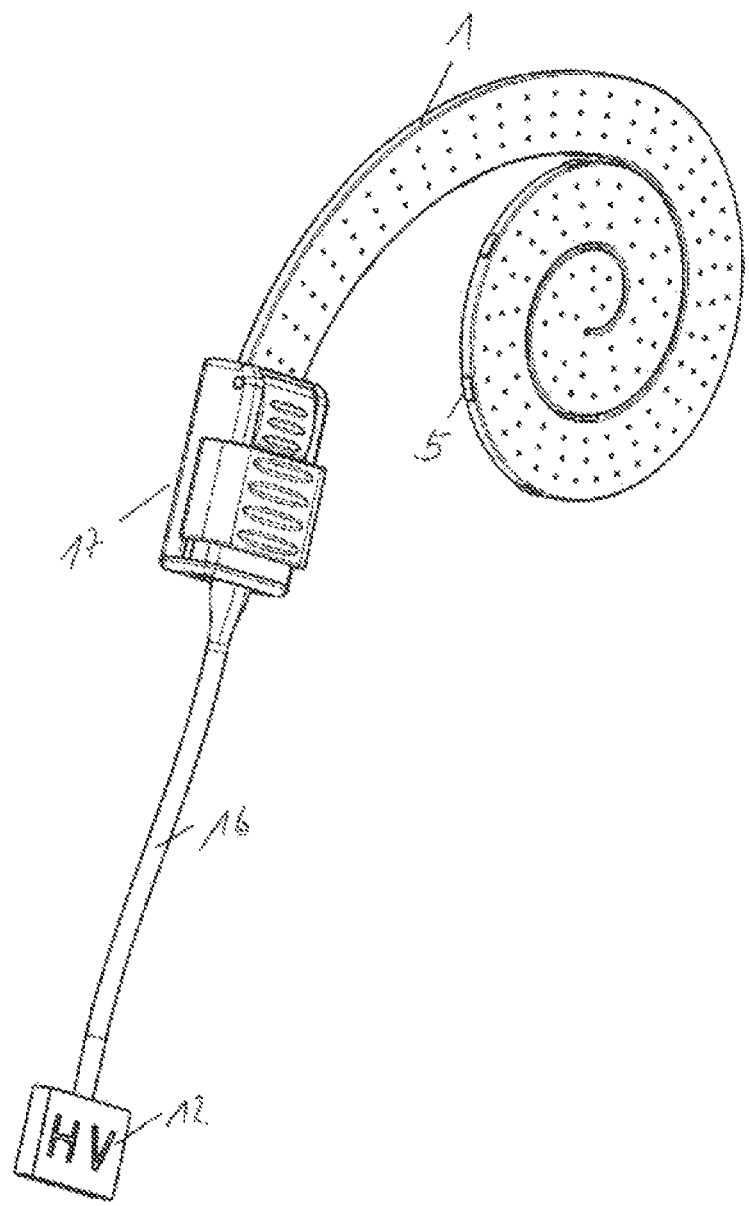
FIG. 10 shows a schematic perspective illustration as shown in FIG. 5 with a contact element with which contact has been made and which is locked.

The position of the contact-making element 17 in which full contact has been made, which contact-making element makes contact with the electrode 14 of the strip 1, is illustrated in FIG. 10.

The high-voltage potential supplied by the high-voltage supply 12 via the high-voltage cable 16 is conducted within the contact-making element in a manner known per se to the insulation displacement contacts 26, with the result that the electrode 14 is connected to a high-voltage potential via the insulation displacement contacts 26.

It can readily be seen that the contact-making implemented by the contact-making elements 17 is simple and safe, but that other contact-making possibilities which are conventional to a person skilled in the art likewise meet all requirements for the safe insulation of the high-voltage potential with respect to discharges as a result of touching contact.

The particular advantage of the electrode arrangement illustrated consists in that the strip can be cut to length at any desired point in a simple manner in order to enable matching of the size of the resting side 6 to the size of a surface to be treated. The process of cutting the strip 1 to length is possible without impairing the function of the electrode 14 because the electrode extends in the longitudinal direction of the strip in said strip, preferably as far as into the central region 3. Contact can be made with the electrode 14 in a simple manner at the end region of the strip having the end face 13 formed by the process of cutting to length, preferably with the aid of a contact-making element 17. The matching of the surface size of the electrode arrangement to the effective surface required for the treatment of a surface can therefore be realized in a simple manner without any complications merely by the strip 1 being cut to length.

The strip 1 preferably consists of a flexible dielectric material, with the result that the electrode arrangement formed by the strip 1 can be matched to irregular three-dimensional surfaces. The short distance between the turns 4 of the strip 1 which is defined by the spacer pieces 5 and is running helically also contributes to this.

It can be seen that through-openings 9 provided in the exemplary embodiments illustrated are not absolutely necessary when, for specific application cases, removal by suction of a fluid from the treatment area which is formed by the interspaces 8 is not required. However, it is known that the removal by suction of fluid can be advantageous, for example, for the treatment of a wound for encouraging sealing of the wound.

The embodiment of the electrode shown in the exemplary embodiments illustrated by means of at least one conductor wire 11 is not absolutely necessary for implementing the invention. It is possible, for example, for the electrode to be implemented by a flexible wire grid embedded in the strip, with it being possible for contact to be made with the wire grid in a similar manner to the conductor wires 11, for example by means of insulation displacement contacts 26 of a contact-making element 17.

Any material which is flexible in an expanding and insulating manner, for example plastics material, can be used for the dielectric material of the strip 1, in particular foamed material, wherein a closed-cell plastic or elastomer foam is preferred because the risk of electrical short circuits by liquids penetrating open pore structures is ruled out thereby. Suitable plasmas material is, for example, foamed polyurethane or silica or a closed-cell natural rubber, without such a list intending to be exclusive.

The invention claimed is:

1. A flexible, flat electrode arrangement for a dielectric barrier gas discharge, comprising
 a central region and a peripheral region,
 a flat electrode for conducting a high voltage potential, and
 a flat dielectric,
  wherein the flat dielectric is, at least in the peripheral region, a flat strip helically wound, and
  wherein the flat electrode has at least one electrical conductor which runs in the longitudinal direction of the wound-up strip and is embedded in the flat dielectric and opens out into an end face of the flat strip so that the flat electrode is covered on all sides by the flat dielectric of the strip with the exception of the end face.

2. The electrode arrangement as claimed in claim 1, wherein the electrical conductor is at least one narrow conductor wire running in the strip from the end face to the central region and from the central region back to the end face.

3. The electrode as claimed in claim 1, wherein the electrical conductor is a conductor wire with a round or oval cross section.

4. The electrode arrangement as claimed in claim 1, further comprising a contact-making element with which the flat electrode makes contact in the region of the end face so that the flat electrode is electrically insulated from the surrounding environment.

5. The electrode arrangement as claimed in claim 4, wherein the contact-making element includes
 a housing which is open on one side and into which the end face of the strip is insertable in such a way that the housing surrounds an upper side, lower side, and narrow sides of an end region of the strip as well as the end face in insulating fashion, and
 insulation displacement contacts for making contact with the flat electrode,
  wherein the insulation displacement contacts cut into the flat dielectric to penetrate into the flat dielectric from one or more of the upper side and the lower side of the flat dielectric.

6. The electrode arrangement as claimed in claim 1, wherein the strip has integrally formed elevations on a lower side, wherein the elevations defines a resting plane and have interspaces which are suitable as a gas space for forming a plasma.

7. The electrode arrangement as claimed in claim 1, wherein the strip has through-openings configured for removal of fluids by suction, wherein the through-openings pass fully through the flat dielectric from a lower side to an upper side.

8. A method of using a flexible, flat electrode arrangement for a dielectric barrier gas discharge,
 wherein the flexible, flat electrode arrangement for a dielectric barrier gas discharge comprises
  a central region and a peripheral region,
  a flat electrode for conducting a high voltage potential, and
  a flat dielectric,
   wherein the flat dielectric is, at least in the peripheral region, a flat strip helically wound, and
   wherein the flat electrode has at least one electrical conductor which runs in the longitudinal direction of the wound-up strip and is embedded in the flat dielectric and opens out into an end face of the flat strip so that the flat electrode is covered on all sides by the flat dielectric of the strip with the exception of the end face;
 wherein the method comprises steps of
  cutting the flat strip to a second length smaller than the first length, the second length being selected to match the area of a surface to be treated with the gas discharge, and
  bringing an end face of the cut flat strip into contact with a contact-making element that fully insulates the flat electrode from the surrounding environment and permits application of a high voltage potential to the flat electrode.

9. The method of claim 8, further comprising steps of
 applying a lower side of the flat dielectric to a wound to be treated, and
 applying the high voltage potential to the flat electrode, the wound's surface forming a mating electrode to the flat electrode embedded in the flat dielectric so that plasma forms over the wound's surface.

* * * * *